US012765862B2

(12) United States Patent
Altmann et al.

(10) Patent No.: US 12,765,862 B2
(45) Date of Patent: Oct. 20, 2026

(54) VISUALIZATION OF 4D ULTRASOUND MAPS

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 11 days.

(21) Appl. No.: 17/357,303

(22) Filed: Jun. 24, 2021

(65) Prior Publication Data

US 2022/0409167 A1 Dec. 29, 2022

(51) Int. Cl.

*A61B 8/08* (2006.01)
*A61B 8/00* (2006.01)
(Continued)

(52) U.S. Cl.

CPC ............ *A61B 8/085* (2013.01); *A61B 8/0883* (2013.01); *A61B 8/12* (2013.01); *A61B 8/4254* (2013.01);
(Continued)

(58) Field of Classification Search

CPC ......... A61B 8/085; A61B 8/0883; A61B 8/12; A61B 8/4254; A61B 8/4488; A61B 8/463;
(Continued)

(56) References Cited

U.S. PATENT DOCUMENTS 6,332,089 B1 12/2001 Acker et al.
6,443,894 B1 9/2002 Sumanaweera et al.
(Continued)

FOREIGN PATENT DOCUMENTS

EP 3666195 6/2020
JP 2004-057379 A 2/2004
(Continued)

OTHER PUBLICATIONS

Wildes, D. et al., "4D ICE: A 2D Array Transducer With Integrated ASIC in a 10-Fr Catheter for Real-Time 3D Intracardiac Echocardiography," in IEEE Transactions on Ultrasonics, Ferroelectrics, and Frequency Control, vol. 63, No. 12, pp. 2159-2173, Dec. 2016, doi: 0.1109/TUFFC.2016.2615602.
(Continued)

*Primary Examiner* — Michael J Carey
*Assistant Examiner* — Maria Christina Talty
(74) *Attorney, Agent, or Firm* — Smith, Gambrell & Russell LLP

(57) ABSTRACT

A medical system includes an ultrasound probe for insertion into an organ of a body and a processor. The ultrasound probe includes (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, and (b) generate a map of the tissue region indicative of respective amounts of motion of tissue locations in the tissue region.

3 Claims, 5 Drawing Sheets

(51) Int. Cl.
*A61B 8/12* (2006.01)
*G06T 7/30* (2017.01)

(52) U.S. Cl.
CPC ............ *A61B 8/4488* (2013.01); *A61B 8/463* (2013.01); *G06T 7/30* (2017.01); *G06T 2207/10132* (2013.01)

(58) Field of Classification Search
CPC ............ G06T 7/30; G06T 2207/10132; G06T 2207/30048
See application file for complete search history.

(56) References Cited

U.S. PATENT DOCUMENTS

| | | | | |
|---|---|---|---|---|
| 6,618,612 | B1 | 9/2003 | Acker et al. | |
| 8,090,429 | B2 | 1/2012 | Vija et al. | |
| 9,980,786 | B2 | 5/2018 | Saul et al. | |
| 10,537,306 | B2 | 1/2020 | Schaer et al. | |
| 10,980,508 | B2 * | 4/2021 | Xu | A61B 6/5247 |
| 11,039,883 | B1 | 6/2021 | Boveja et al. | |
| 2002/0065455 | A1 | 5/2002 | Ben-Haim et al. | |
| 2003/0013957 | A1 * | 1/2003 | Bjaerum | A61B 8/08 600/437 |
| 2003/0120150 | A1 | 6/2003 | Govari | |
| 2004/0068178 | A1 | 4/2004 | Govari et al. | |
| 2005/0020917 | A1 | 1/2005 | Scherch | |
| 2005/0228278 | A1 | 10/2005 | Chalana et al. | |
| 2007/0073135 | A1 | 3/2007 | Lee et al. | |
| 2007/0106147 | A1 | 5/2007 | Altmann et al. | |
| 2008/0039723 | A1 | 2/2008 | Suri | |
| 2008/0300487 | A1 | 12/2008 | Govari et al. | |
| 2009/0161938 | A1 | 6/2009 | Shekhar et al. | |
| 2010/0041949 | A1 * | 2/2010 | Tolkowsky | A61B 5/742 600/117 |
| 2010/0099991 | A1 | 4/2010 | Snyder | |
| 2011/0166455 | A1 * | 7/2011 | Cully | A61B 8/4245 600/463 |
| 2012/0245458 | A1 | 9/2012 | Gogin | |
| 2012/0310064 | A1 * | 12/2012 | McGee | A61B 8/12 600/373 |
| 2013/0090554 | A1 * | 4/2013 | Zvuloni | A61B 5/061 600/424 |
| 2016/0007970 | A1 * | 1/2016 | Dufour | A61B 8/085 600/437 |
| 2016/0262720 | A1 * | 9/2016 | Henderson | A61B 8/466 |
| 2017/0020486 | A1 | 1/2017 | Salcudean et al. | |
| 2017/0120080 | A1 * | 5/2017 | Phillips | A61B 34/25 |
| 2018/0342072 | A1 * | 11/2018 | Raudins | A61B 8/4245 |
| 2019/0216429 | A1 | 7/2019 | Sakai et al. | |
| 2019/0336110 | A1 | 11/2019 | Kustra | |
| 2019/0380687 | A1 | 12/2019 | Peled et al. | |
| 2020/0037983 | A1 | 2/2020 | Poland | |
| 2020/0061340 | A1 | 2/2020 | Mixter et al. | |
| 2020/0113540 | A1 * | 4/2020 | Gijsbers | A61B 8/5253 |
| 2020/0170617 | A1 * | 6/2020 | de Vaan | A61B 8/0891 |
| 2020/0214662 | A1 | 7/2020 | Konofagou et al. | |
| 2021/0068788 | A1 * | 3/2021 | Yang | A61B 8/00 |
| 2021/0275142 | A1 | 9/2021 | Sudol et al. | |
| 2023/0005153 | A1 * | 1/2023 | Gupta | G06T 7/0012 |
| 2024/0350116 | A1 | 10/2024 | Clark | |

FOREIGN PATENT DOCUMENTS

| | | | |
|---|---|---|---|
| JP | 2007-144150 | A | 6/2007 |
| JP | 2008-302220 | A | 12/2008 |
| JP | 2011-217775 | A | 11/2011 |
| JP | 2015-173899 | A | 10/2015 |
| JP | 2019-122539 | A | 7/2019 |
| JP | 2019-528977 | A | 10/2019 |
| JP | 2019-528981 | A | 10/2019 |
| JP | 2019-217276 | A | 12/2019 |
| JP | 2020-062072 | A | 4/2020 |
| WO | WO9605768 | | 2/1996 |

OTHER PUBLICATIONS

Bunting, Ethan, et al. "Cardiac lesion mapping in vivo using intracardiac myocardial elastography." https://www.ncbi..nlm.nlh.gov/pmc/articles/PMC5747324/pdf/nihms919938.pdf abstract; figures 1-7.

Extended European Search Report dated Nov. 17, 2022 from corresponding EP Application: 22180642.5-1126.

Glabber et al., "Combined Visualization of Wall Thickness and Wall Shear Stress for the Evaluation of Aneurysms", IEEE Transactions on Visualization and Computer Graphics, vol. 20, No. 2, Dec. 31, 2014, pp. 2506-2515.

Extended European Search Report and Search Opinion received for EP Application No. 25201913.8, mailed on Dec. 12, 2025, 10 pages.

* cited by examiner

VISUALIZATION OF 4D ULTRASOUND MAPS

FIELD OF THE INVENTION

The present invention relates generally to medical visualizing methods, and particularly to visualizing ultrasound data acquired using an intra-body medical ultrasound probe.

BACKGROUND OF THE INVENTION

Various ultrasound visualization techniques to assess organ functioning within the body have been previously proposed in the patent literature. For example, U.S. Patent Application Publication 2020/0214662 describes systems and methods for generating an electromechanical map. The methods include obtaining ultrasound data comprising a series of consecutive image frames and radio frequency (RF) signals corresponding to a tissue location in the heart. Displacements and strains are measured based on the ultrasound data to determine an electromechanical activation in the location. The ultrasound data is converted into a series of isochrone maps, and the series of isochrone maps is combined, to generate the electromechanical map. The electromechanical map illustrates the electromechanical activation and internal wall structures of the heart.

As another example, U.S. Patent Application Publication 2010/0099991 describes an ultrasonic diagnostic imaging system that produces 3D images of blood flow which depict both the location of blood pools and flow velocity in one image. B mode data is acquired over a volumetric region and inverted to a range of grayscale value which highlights anechoic regions relative to regions of strong echo returns. Flow data is acquired over the same volumetric region and both data sets are volume rendered. The two volume renderings are then merged into a single 3D image in which the B mode pixel values are tinted in accordance with flow at the pixel locations.

U.S. Pat. No. 8,090,429 describes systems and methods for co-registering, displaying and quantifying images from numerous different medical modalities, such as CT, MRI and SPECT. In this approach, co-registration and image fusion is based on multiple user-defined Regions-of-Interest (ROI), which may be subsets of entire image volumes, from multiple modalities, where each ROI may depict data from different image modalities. The user-selected ROI of a first image modality may be superposed over or blended with the corresponding ROI of a second image modality, and the entire second image may be displayed with either the superposed or blended ROI.

There remains a need however for improved means for simultaneously presenting a physician or operator with ultrasound images, such as 4D ultrasound images, and correlated visual data, such as electrophysiological data.

SUMMARY OF THE INVENTION

An embodiment of the present invention that is described hereinafter provides a medical system including an ultrasound probe for insertion into an organ of a body and a processor. The ultrasound probe includes (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, and (b) generate a map of the tissue region indicative of respective amounts of motion of tissue locations in the tissue region.

In some embodiments, the processor is further configured to identify, based on the amounts of motion of the tissue locations, that tissue at one or more of the tissue locations includes scar tissue, and present the map to a user, with an indication of the identified scar tissue.

In some embodiments, the processor is configured to indicate the identified scar tissue using a graphically encoded level of motion of the tissue.

In an embodiment, the graphically encoded level of motion includes a color-coded level of motion.

In another embodiment, the processor is configured to identify the scar tissue by comparing the amounts of tissue motion to a threshold value.

There is additionally provided, in accordance with another embodiment of the present invention, a medical system including an ultrasound probe for insertion into an organ of a body and a processor. The ultrasound probe includes (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) isolate inner wall images and outer wall images of the region one from the other, (c) apply different graphical encodings to the inner wall images and the outer wall images, (d) overlay the inner wall images and the outer wall images to generate a combined image, (e) display the combined image to a user, and (f) adjust a transparency of one or both of the overlaid inner wall images and outer wall images.

In some embodiments, the different graphical encodings are different color palettes.

In some embodiments, the inner wall images and outer wall images of the region are an endocardium image and a respective epicardium image of a same portion of a heart.

There is further provided, in accordance with another embodiment of the present invention, a medical system including an ultrasound probe for insertion into an organ of a body and a processor. The ultrasound probe includes (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) generate a map of the tissue region, and incorporate in the map an icon indicative of a type of the ultrasound probe used for acquiring the ultrasound images, and (c) present the map to a user with an indication of the type of the ultrasound probe.

In some embodiments, the type of the ultrasound probe is one of an ultrasound probe including a one-dimensional (1D) array and an ultrasound probe including a two-dimensional (2D) array of transducers.

There is furthermore provided, in accordance with another embodiment of the present invention, a medical system including an ultrasound probe for insertion into an organ of a body and a processor. The ultrasound probe includes (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) generate an ultrasound image of the tissue region, (c) upload, to a graphical user interface, (i) the generated ultrasound image and (ii) one or more additional images of the tissue region acquired by one or more respective non-ultrasound medical imaging modalities, (d) generate a combined image by weighting respective contributions of the ultrasound image and of the or more additional images, and (e) display the combined image to a user.

In some embodiments, the processor is further configured to adjust the combined image by adjusting the weighting.

There is further yet provided, in accordance with another embodiment of the present invention, a medical system including a display and a processor. The display is configured to display images to a user. The processor is configured to (a) register two or more different representations of a tissue region, acquired in accordance with a medical modality, with one another, (b) generate a combined image by weighting respective contributions of the representations, and (c) display the combined representation to the user using the display.

In some embodiments, the representations include electrophysiological maps.

In some embodiments, the electrophysiological maps include local activation time (LAT) or bipolar voltage maps.

There is additionally provided, in accordance with another embodiment of the present invention, a method, including inserting an ultrasound probe into an organ of a body, the ultrasound probe including a two-dimensional (2D) ultrasound transducer array, and a sensor configured to output signals indicative of a position, direction and orientation of the 2D ultrasound transducer array inside the organ. Using the signals output by the sensor, multiple ultrasound images of a tissue region are registered with one another, that are acquired over a given time duration by the 2D ultrasound transducer array. A map of the tissue region is generated, that is indicative of respective amounts of motion of tissue locations in the tissue region.

There is further provided, in accordance with another embodiment of the present invention, a method, including inserting an ultrasound probe into an organ of a body, the ultrasound probe including a two-dimensional (2D) ultrasound transducer array, and a sensor configured to output signals indicative of a position, direction and orientation of the 2D ultrasound transducer array inside the organ. Using the signals output by the sensor, multiple ultrasound images of a tissue region are registered with one another, that are acquired over a given time duration by the 2D ultrasound transducer array. Inner wall images and outer wall images of the region are isolated one from the other. Different graphical encodings are applied to the inner wall images and the outer wall images. The inner wall images and the outer wall images are overlayed to generate a combined image. The combined image is displayed to a user. A transparency is adjusted, of one or both of the overlaid inner wall images and outer wall images.

There is additionally more provided, in accordance with another embodiment of the present invention, a method, including inserting an ultrasound probe into an organ of a body, the ultrasound probe including a two-dimensional (2D) ultrasound transducer array, and a sensor configured to output signals indicative of a position, direction and orientation of the 2D ultrasound transducer array inside the organ. Using the signals output by the sensor, multiple ultrasound images of a tissue region are registered with one another, that are acquired over a given time duration by the 2D ultrasound transducer array. A map of the tissue region is generated, and an icon is incorporated in the map, that is indicative of a type of the ultrasound probe used for acquiring the ultrasound images. The map is presented to a user with an indication of the type of the ultrasound probe.

There is furthermore provided, in accordance with another embodiment of the present invention, a method, including inserting an ultrasound probe into an organ of a body, the ultrasound probe including a two-dimensional (2D) ultrasound transducer array, and a sensor configured to output signals indicative of a position, direction and orientation of the 2D ultrasound transducer array inside the organ. Using the signals output by the sensor, multiple ultrasound images of a tissue region are registered with one another, that are acquired over a given time duration by the 2D ultrasound transducer array. An ultrasound image of the tissue region is generated. Uploaded to a graphical user interface, are (i) the generated ultrasound image and (ii) one or more additional images of the tissue region acquired by one or more respective non-ultrasound medical imaging modalities. A combined image is generated by weighting respective contributions of the ultrasound image and of the or more additional images. The combined image is displayed to a user.

There is further yet provided, in accordance with another embodiment of the present invention, a method, including registering two or more different representations of a tissue region, acquired in accordance with a medical modality, with one another. A combined image is generated by weighting respective contributions of the representations. The combined representation is displayed to the user.

The present invention will be more fully understood from the following detailed description of the embodiments thereof, taken together with the drawings in which:

DETAILED DESCRIPTION OF EMBODIMENTS

Overview

Figure 1:
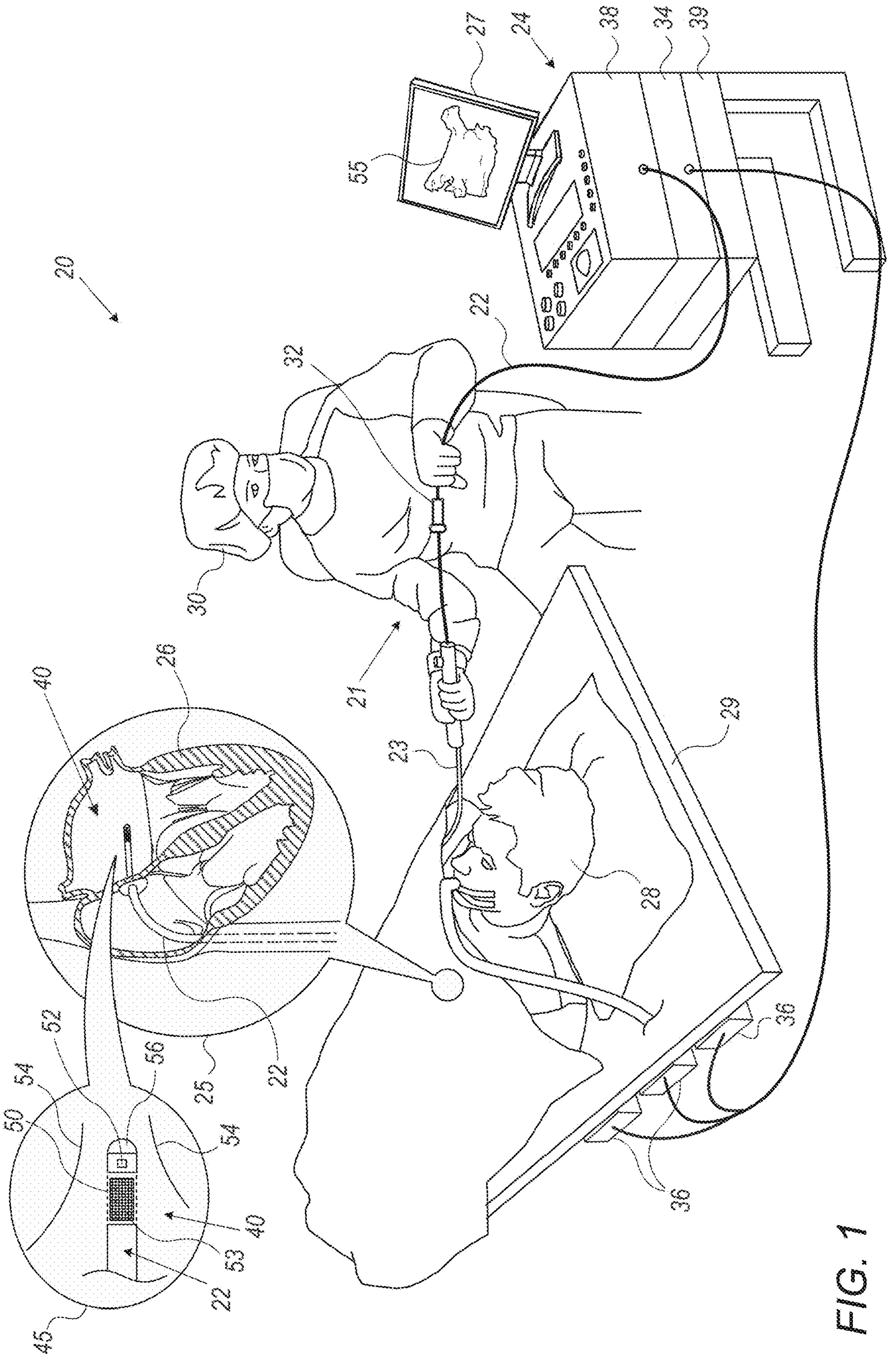
FIG. 1 is a schematic, pictorial illustration of a catheter-based ultrasound imaging system using a catheter with a distal end assembly comprising a 2D ultrasound-array and a location sensor, in accordance with an embodiment of the present invention.

Embodiments of the present invention that are described hereinafter provide methods and systems that use a probe, such as a catheter, having a two-dimensional (2D) array of ultrasound transducers for producing three-dimensional (3D) or four-dimensional (4D) ultrasound images. In the present context, the term "3D ultrasound image" refers to an ultrasound image that represents a certain volume in three dimensions. The term "4D ultrasound catheter" refers to a catheter incorporating a 2D array of ultrasound transducers. The term "4D ultrasound image" refers to a time series of 3D ultrasound images of a certain volume acquired by the 2D array. A 4D image can be regarded as a 3D movie, the fourth dimension being time. Another way of describing a 4D image (or rendering) is as a time-dependent 3D image (or rendering). Where used in the heart, a 4D ultrasound catheter may be referred to as "4D Intracardiac Echocardiography (ICE)" catheter.

In the disclosed embodiments, the catheter also comprises an integral location sensor, such as a magnetic position sensor, that is pre-registered with the 2D array. The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber. Because of the integral location sensor, the spatial coordinates of every voxel in the imaged section is known based on the known relative position and orientation on the catheter shaft between the location sensor and the 2D array.

It may be possible to generate a 4D ultrasound rendering, and, at the same time, an electrophysiological (EP) rendering, of a portion of the heart. However, it is difficult for a physician to correlate the two separate renderings.

Some embodiments of the present invention overlay EP data, such as local activation times (LATs) or bipolar voltages, on a 4D ultrasound image or 3D rendering, the 3D/4D representation generated by a 4D ultrasound catheter. Because the 4D catheter has an integral location sensor and its pre-registration with the 2D array, the two entities, i.e., the EP values and the ultrasound image, are automatically registered in the combined image so that registration of the EP parameters with the ultrasound image is not required.

For example, the 4D ultrasound image may show 3D details of a wall of a heart chamber, as well as movement of the wall, so that the combined image shows these details as well as the electrical activity (e.g., the EP data). This will be apparent, for example, in a wall tissue region of a scar, where the mechanical movement of the tissue is different from that of surrounding unscarred tissue, and the electrical propagation in the region of the scar is different from that of unscarred tissue. The combined image may enhance a capability of a clinician to diagnose and decide on a treatment of a cardiac problem related to scars. In another embodiment, a user may import strain information from the ultrasound images and use a processor to compare and/or display the imported strain information with the electrical activity. This enables correlation between mechanical and electrical heart functionality.

Standard ultrasound images of surfaces of the walls of a heart chamber, i.e., the endocardium and the epicardium images, can be acquired. However, the different surfaces are hard to comprehend, even though the images are somewhat displaced in an ultrasound image, as both surfaces depicted in grayscale means it is impossible to clearly see the two surfaces. Typically, the endocardium and epicardium images are obtained by a processor segmenting the volume data acquired by the ultrasound probe. If an anatomical map exists, the processor may use the map to identify the different surfaces.

Some embodiments of the present invention allow a user of the 4D ultrasound catheter to apply different color palettes to the two images of the surfaces of the chamber wall. This renders the two surfaces clearly differentiable, by, for example, a processor overlaying a colored endocardium image on an epicardium image that is colored differently. The user may also adjust the transparency of the overlay to further enhance the combined image displayed.

As the ultrasound catheter is registered to the mapping location system, the system can use this pre-acquired knowledge to color the multiple structures (e.g., the endocardium and the epicardium) in the ultrasound image with different color scales.

Moreover, each area in each of the ultrasound images can be colored with a unique color scale according to its functionality, or used definition, such as using different color palette comprising, for example, warm colors or cold colors. For example, after mapping the right atrium, the ultrasound image area of the right atrium can be colored differently (with different color scales, such as red with different intensity according to the gray levels, or different color palettes, such as warm colors vs. cold colors for the endocardium and the epicardium images).

Icons for ultrasound catheters do not differentiate between the types of ultrasound catheter used. For example, in contrast to a 1D catheter which produces an ultrasound fan, 2D catheters produce an ultrasound wedge. In an embodiment, to inform a reviewer how ultrasound data was acquired, a processor selects a specific icon to incorporate into an existing 3D surface ultrasound rendering. In this embodiment the processor may display an icon of a 2D catheter producing 4D images, by incorporating a wedge icon in a 3D/4D rendering.

In many medical procedures, images having different functionalities may be acquired, e.g., using different imaging modalities, and, for comparison purposes, these images may be registered. Since they are registered, the images may be combined with each other so that the different elements on the images may be viewed simultaneously. However, each image typically carries much visual information, so that combining the images may quickly lead to information overload.

Some embodiments of the present invention provide a graphical user interface (GUI) that allows a reviewer to generate and adjust a combined image by weighting the contributions of the separate images to the combined image.

In an example, three available images are to be considered that are all registered one with other (e.g., to a coordinate system of a tracking system): a computerized tomography (CT) image, a magnetic resonance imaging (MRI) image, and an ultrasound (US) image. Using the GUI to weight the CT, MRI and US images, the reviewer combines the three images into one. One disclosed image weighting model, which a GUI may apply using a processor, is based on the assumption that the images are positioned at the apices of a triangle, where the triangle is used as a weighting selector. To this end, the reviewer can move a cursor within the triangle to select the weight applied to each image.

Note that the different images to be weighted and combined do not necessarily have to be of different modalities. Rather, these images can be different representations of a tissue region acquired by a same medical modality. For example, an EP mapping modality can generate a first representation of LATs in a color map, and a second representation of a bipolar voltages map provided in gray scales. Such a combined EP representation may possess enhanced clinical significance.

SYSTEM DESCRIPTION

FIG. 1 is a schematic, pictorial illustration of a catheter-based ultrasound imaging system 20 using a catheter 21 with a distal end assembly 40 comprising a 2D ultrasound array 50 and a location sensor 52, in accordance with an embodiment of the present invention. Integral location sensor 52 is pre-registered with the 2D array 50 of catheter 21.

Specifically, sensor 52 is configured to output signals indicative of a position, direction and orientation of the 2D ultrasound transducer array 50 inside the organ. A processor of the system is configured to register multiple ultrasound image sections using the signal output by the sensor acquired by the 2D ultrasound transducer array 50, one with the other.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the embodiment described herein, catheter 21 is used for ultrasound-based diagnostic purposes, although the catheter may be further used to perform therapy, such as electrical sensing and/or ablation of tissue in heart 26, using, for example, a tip electrode 56.

Physician 30 navigates distal end assembly 40 of catheter 21 to a target location in heart 26 by manipulating shaft 22 using a manipulator 32 near the proximal end of the catheter.

In an embodiment, 2D ultrasound-array 50, shown in detail in an inset 25, is configured to image a left atrium of heart 26.

As seen in an inset 45, ultrasound array 50 comprises a 2D array 50 of multiple ultrasound transducers 53. Inset 45 shows ultrasound array 50 navigated to an ostium 54 of a pulmonary vein of the left atrium. In this embodiment, 2D array 50 is an array of 32×64 US transducers. The 2D array is able to image a section of the inner wall of the ostium. Because of the integral location sensor, and its pre-registration with the 2D array, the spatial coordinates of every pixel in the imaged section are known by the system. An example of a suitable 2D array is described in D. Wildes et al., "4-D ICE: A 2-D Array Transducer With Integrated ASIC in a 10-Fr Catheter for Real-Time 3-D Intracardiac Echocardiography," in IEEE Transactions on Ultrasonics, Ferroelectrics, and Frequency Control, vol. 63, no. 12, pp. 2159-2173, December 2016, doi: 10.1109/TUFFC.2016.2615602, which is incorporated herein by reference in its entirety.

Control console 24 comprises a processor 39, typically a general-purpose computer, with suitable front end and interface circuits 38 for receiving signals from catheter 21, as well as for, optionally, applying treatment via catheter 21 in heart 26 and for controlling the other components of system 20. Console 24 also comprises a driver circuit 34, configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

Exemplary catheters and imaging assemblies that enable deflection and rotation are described in detail in U.S. Pat. Nos. 9,980,786; 10,537,306; and U.S. Patent Publication No. 2020-0061340 A1, whose disclosures are all incorporated herein by reference.

In some embodiments, processor 39 may be configured to operate array 52 in a "sweeping mode" to image a whole cardiac camber, as described below. In an embodiment, the imaged cardiac chamber (e.g., a left atrium) is presented to physician 30 by processor 39 on a monitor 27, e.g., in as a volume rendering 55.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations.

Rendering and Visualization of 4D Ultrasound Maps

Figure 2:
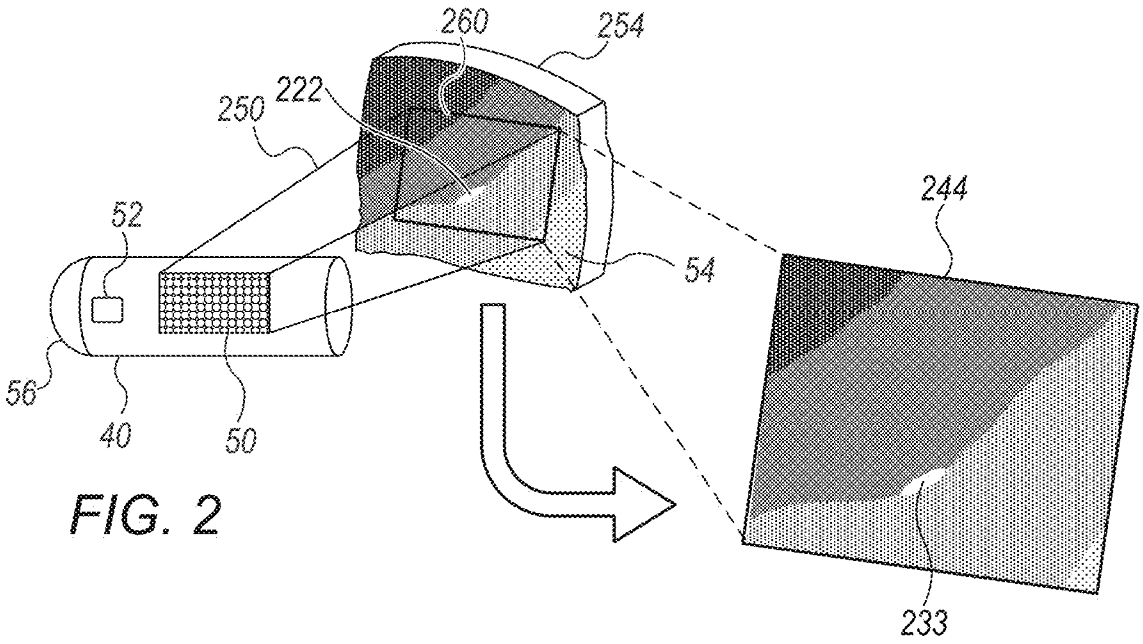
FIG. 2 is a schematic, pictorial illustration of a visualization of a scarred tissue region in an inner wall section of an organ imaged using the ultrasound system of FIG. 1, in accordance with an embodiment of the present invention.

FIG. 2 is a schematic, pictorial illustration of a visualization of a scarred tissue region 222 in an inner wall 54 section 260 of an organ 254 imaged using ultrasound system 20 of FIG. 1, in accordance with an embodiment of the present invention. The acquisition is performed using catheter 21 of system 20 of FIG. 1. As seen, a 3D wedge 250 mode of acquisition enables simultaneous acquisition of the 2D section 260. Using location sensor 52, the geometry of ultrasound wedge 250 can be defined in a coordinate system of the location tracking system of system 20.

Using the registration, processor 39 derives a tissue color-coded motion map 244 from the acquisition, comprising a color-coded visualized scarred region 233. The processor distinguishes a scar by estimating that the mechanical movement of the tissue therein is different (typically lower or absent) from that of surrounding non-scarred tissue. In an embodiment, the processor graphically encodes (e.g., marks, or color codes), also in real time, e.g., on the video image that is displayed, the amounts of motion, to distinguish immobile areas that may be scarred tissue.

In an embodiment, the processor is configured to identify scarred tissue by comparing the level of tissue motion to a threshold value of expected amount of motion of a healthy tissue.

Figure 3:
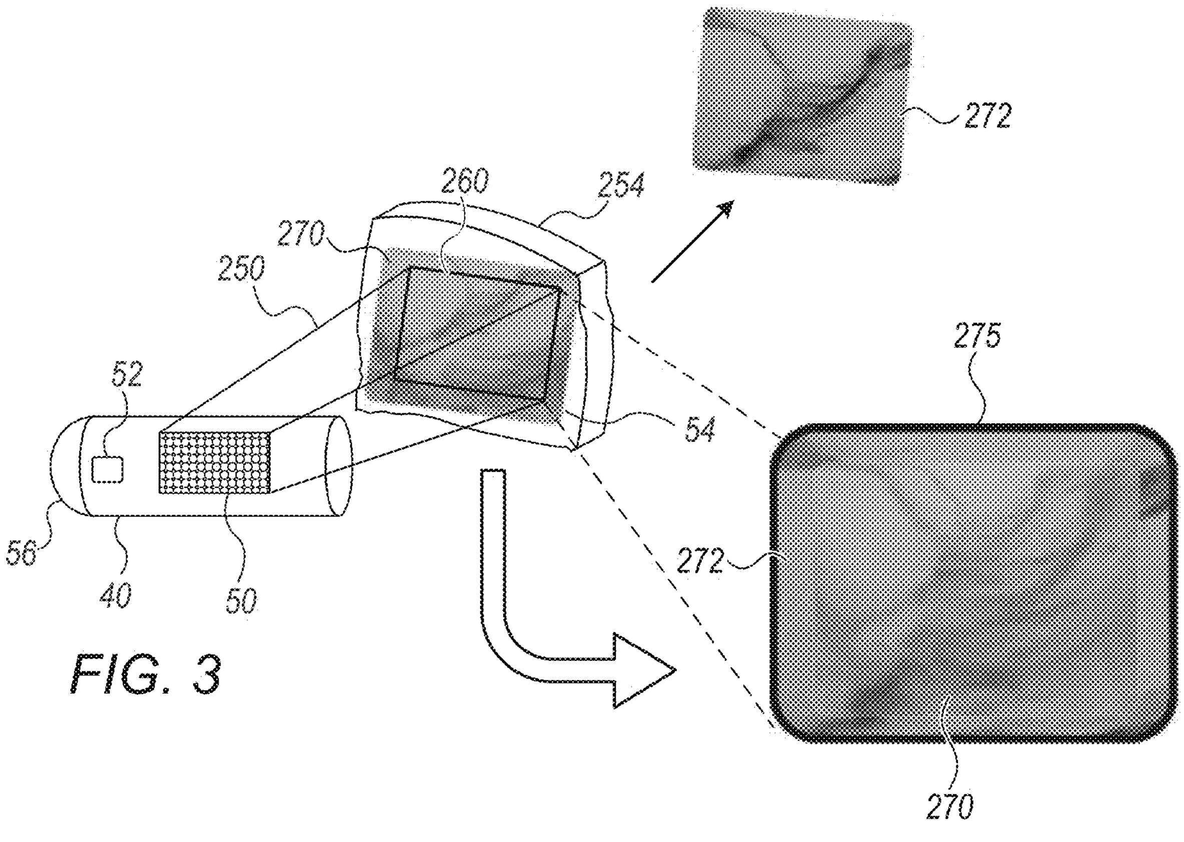
FIG. 3 is a schematic, pictorial illustration of ultrasound intracardiac acquisition using the system of FIG. 1, followed by derivation of a combined tissue motion map overlaying an endocardium image over a respective epicardium image, in accordance with embodiments of the present invention.

FIG. 3 is a schematic, pictorial illustration of ultrasound intracardiac acquisition using system 20 of FIG. 1, followed by derivation of a combined tissue motion map 275 overlaying an endocardium image 270 and a respective epicardium 272 image, in accordance with embodiments of the present invention.

In an embodiment, using location information from sensor 52, endocardium image 270 and its respective epicardium image 272 are extracted from an ultrasound acquisition/conventional image (e.g., the cardiac surfaces shown by images 270 and 272 are isolated from one another using an algorithm). Consider, for example, a scenario in which the catheter is in a cardiac chamber, or a user has selected a point in the chamber, or an anatomical map (such as a CARTO™ anatomical map) already exists, and its center mass can be used. In an embodiment, the processor may apply an algorithm that extends a simulated beam ray from the selected point, such that the ray intersects the first surface and then the second border. Existing algorithms that are used today for segmentation of CT and MRI 3D scans can be also utilized, for example multi-thresholding based on statistical local and global parameters, mathematical morphology, and image filtering.

Subsequently, imaged section 260 is color coded in each of the ultrasound images with a unique color scale according to its functionality (e.g., amount of movement). The color code can be correlated to velocity, strain, voltage, thickness, local activation time and/or using another definition, for example by using different color scales, e.g., warm colors vs. cold colors.

In the shown example, the user may also adjust the transparency of the overlay 270 to further enhance the combined displayed image.

Figure 4:
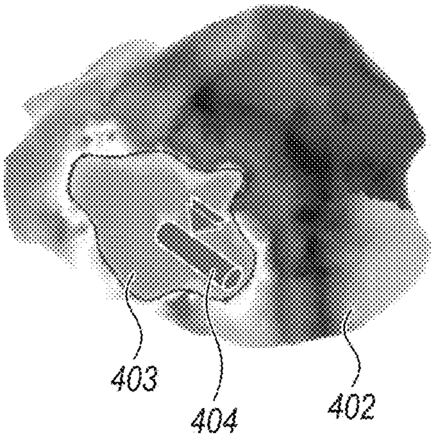
FIG. 4 is a schematic, pictorial illustration showing the incorporation of an icon into a 3D rendering, the icon indicative of the type of ultrasound catheter used in generating the rendering, in accordance with embodiments of the present invention.

FIG. 4 is a schematic, pictorial illustration showing the incorporation of an icon 402 into a 3D rendering 404, where icon 402 is indicative of the type of ultrasound catheter used to generate the rendering, in accordance with embodiments of the present invention. Specifically, FIG. 4 shows a 3D rendering of a cardiac chamber 402, derived using system 20 of FIG. 1, that incorporates an icon 404 indicative of the type of ultrasound catheter 21.

In the shown embodiment, a region 403 of the surface rendering is made transparent by processor 39, which further incorporates therein icon 404, to show a wedge beam of 2D catheter 21 that was used for the intracardiac acquisition.

Figure 5:
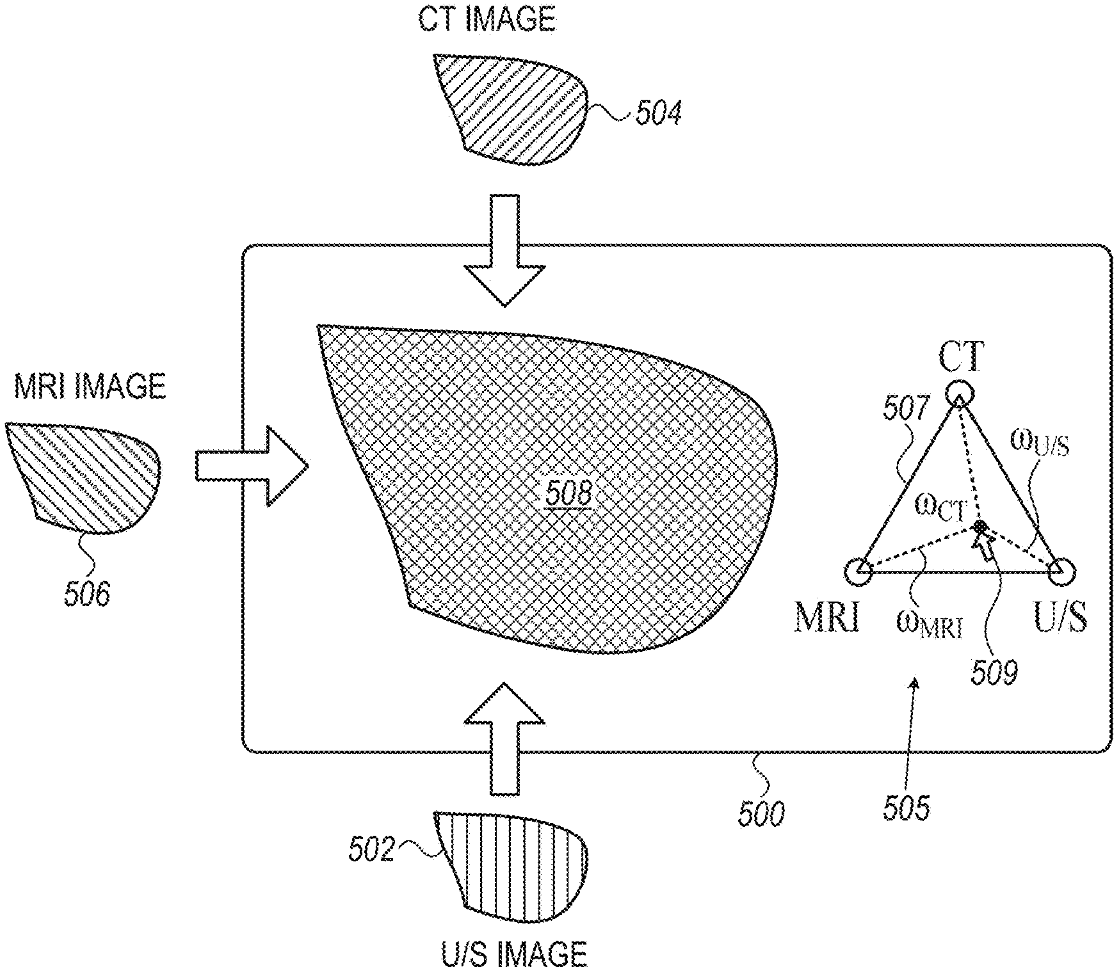
FIG. 5 is a schematic, pictorial illustration of a graphical user interface (GUI) configured to generate and display a combined image made by weighting images from different imaging modalities, in accordance with embodiments of the present invention.

FIG. 5 is a schematic, pictorial illustration of a graphical user interface (GUI) 500 configured to generate and display a combined image 508 made by weighting images (502, 504 and 506) from different imaging modalities, in accordance with embodiments of the present invention. In other embodiments, the different images do not necessarily have to all be from different imaging modalities. For example, GUI 500 may combine EP maps with an image of an imaging modality combining an LAT map, bipolar voltage map and an ultrasound rendering.

In the shown embodiment, GUI 500 allows a reviewer of combined image 508 to select the display weighting that is applied to three images, a computerized tomography (CT) image 504, a magnetic resonance imaging (MRI) 506, and an ultrasound (US) image 502 that are all registered one with the other.

A disclosed image weighting algorithm 505 used with GUI 500 assumes the images are positioned at the apices of a triangle 507, and a reviewer can move a cursor 509 within the triangle area to select the relative weights ω applied to each image. In one embodiment the weights are normalized by the sum of weights that is kept equal to one, $\omega_{CT}+\omega_{MRI}+\omega_{U/S}=1$. In another embodiment, the weights are normalized by the sum of squares of the weights and kept equal to one, $\omega^2_{CT}+\omega^2_{MRI}+\omega^2_{U/S}=1$.

GUI 500 and method of weighting using a triangle area are shown by way of example. Other implementations are possible, for example, using a circle or a polygon to represent the image-weighting space.

Methods of Visualization of 4D Ultrasound Maps

Figure 6:
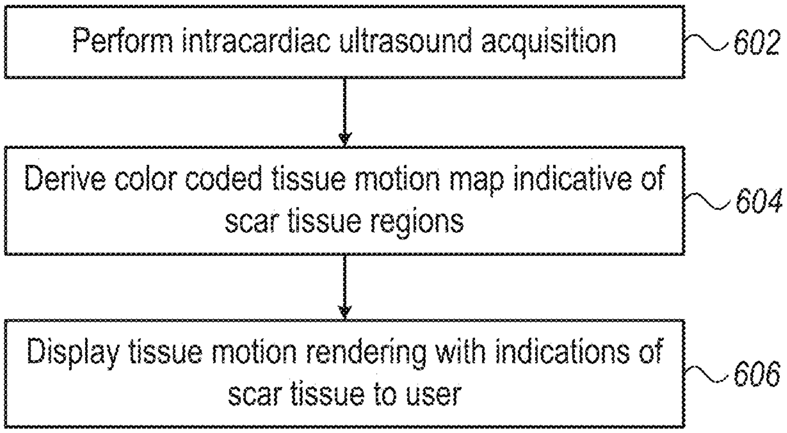
FIG. 6 is a flow chart that schematically illustrates a method for deriving and displaying the results of FIG. 2, in accordance with an embodiment of the present invention.

FIG. 6 is a flow chart that schematically illustrates a method for deriving and displaying the results of FIG. 2, in accordance with an embodiment of the present invention. The procedure begins by performing an ultrasound acquisition inside a cardiac chamber, such as shown in FIG. 1, at a 4D ultrasound acquisition step 602.

Next, at a tissue motion map derivation step 604, processor 39 derives a color-coded tissue-motion map that is indicative of scarred tissue regions, such as rendering 244 described in FIG. 2. To this end, the generated map of the tissue region is indicative of respective amounts of motion of tissue locations in the tissue region. the processor identifies, based on the amounts of motion of the tissue locations, that tissue at one or more of the tissue locations comprises scar tissue.

At a rendering displaying step 606, processor 39 displays a cardiac tissue motion rendering of step 602 to a user, such as shown with rendering 55 on monitor 27 of FIG. 1. The presentation may include adding graphical indication, e.g., by coloring or patterning on map the scarred area, or by placing visual markings, to scarred regions encoded in rendering 244.

The flow chart of FIG. 6 is brought purely by example. In other embodiments, as another example, processor 39 performs pattern coding instead of color coding.

Figure 7:
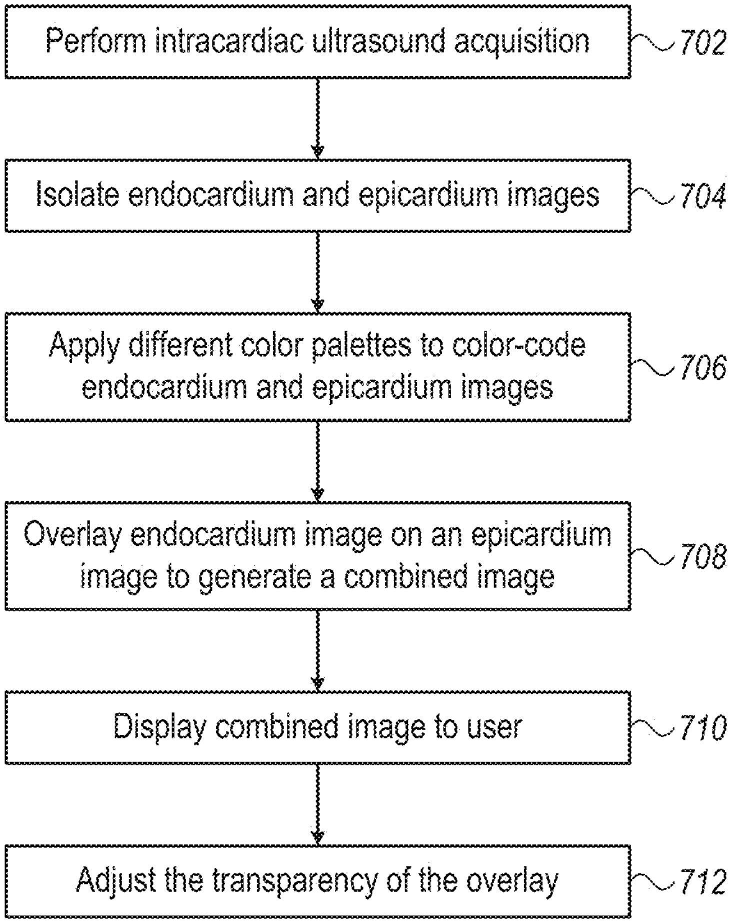
FIG. 7 is a flow chart that schematically illustrates a method for deriving and displaying the results of FIG. 4, in accordance with an embodiment of the present invention.

FIG. 7 is a flow chart that schematically illustrates a method for deriving and displaying the results of FIG. 4, in accordance with an embodiment of the present invention. The procedure begins by performing an ultrasound acquisition inside a cardiac chamber, such as shown in FIG. 1, at a 4D ultrasound acquisition step 702.

Next, processor 39 isolates endocardium and respective epicardium images of a same imaged section, such as images 270 and 272 of imaged section 360, shown in FIG. 3, at surfaces image extraction step 704.

In a color-coding step 706, processor 39 applies different color palettes (e.g., red-based and blue-based) to images 270 and 272, for example, to indicate amounts of motion.

At image overlaying step 708, processor 39 overlays endocardium image 270 on epicardium image 272 to generate a combined image 275.

Processor 39 displays combined image 275 to a user at a displaying step 710. Finally, at an adjustment step 712, the user adjusts a level of transparency of image 270 to make combined image 275 more visible.

Figure 8:
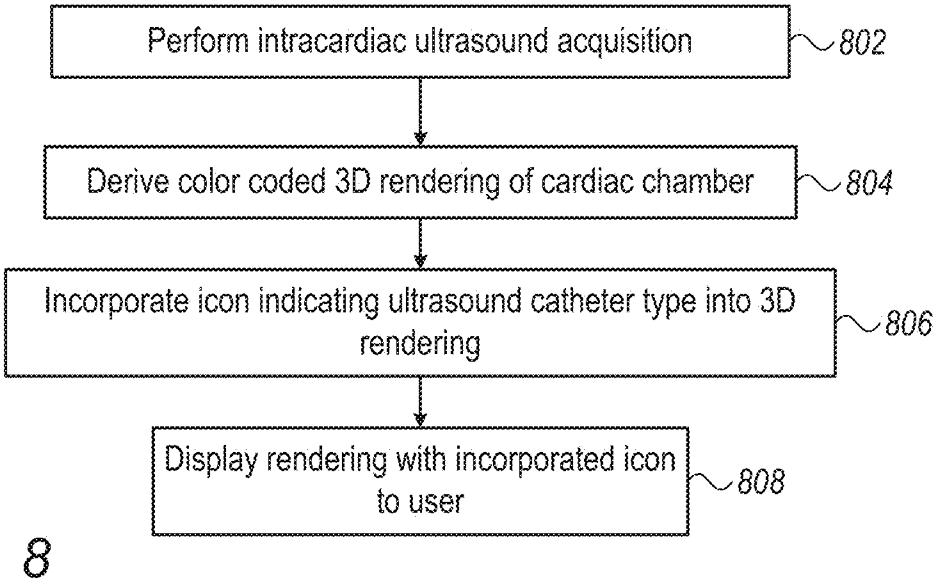
FIG. 8 is a flow chart that schematically illustrates a method for showing the incorporation of an icon into a 3D rendering, where the icon is indicative of the type of ultrasound catheter used in generating the rendering, in accordance with embodiments of the present invention.

FIG. 8 is a flow chart that schematically illustrates a method for showing the incorporation of icon 404 into a 3D rendering 402, where the icon is indicative of the type of ultrasound catheter 21 used in generating the rendering, in accordance with embodiments of the present invention. The procedure begins by performing an ultrasound acquisition inside a cardiac chamber, such as shown in FIG. 1, at a 4D ultrasound acquisition step 802.

Next, processor 39 derives color coded 3D rendering of cardiac chamber 402, shown in FIG. 4, at a 3D rendering step 804.

At icon incorporation step 806, processor 39 incorporates icon 404 that shows a wedge ultrasound beam, indicating that a 2D ultrasound catheter, such as catheter 21, was used for acquiring the data at step 802.

Finally, at a displaying step 808, processor 39 displays the icon-incorporated rendering to a user.

Figure 9:
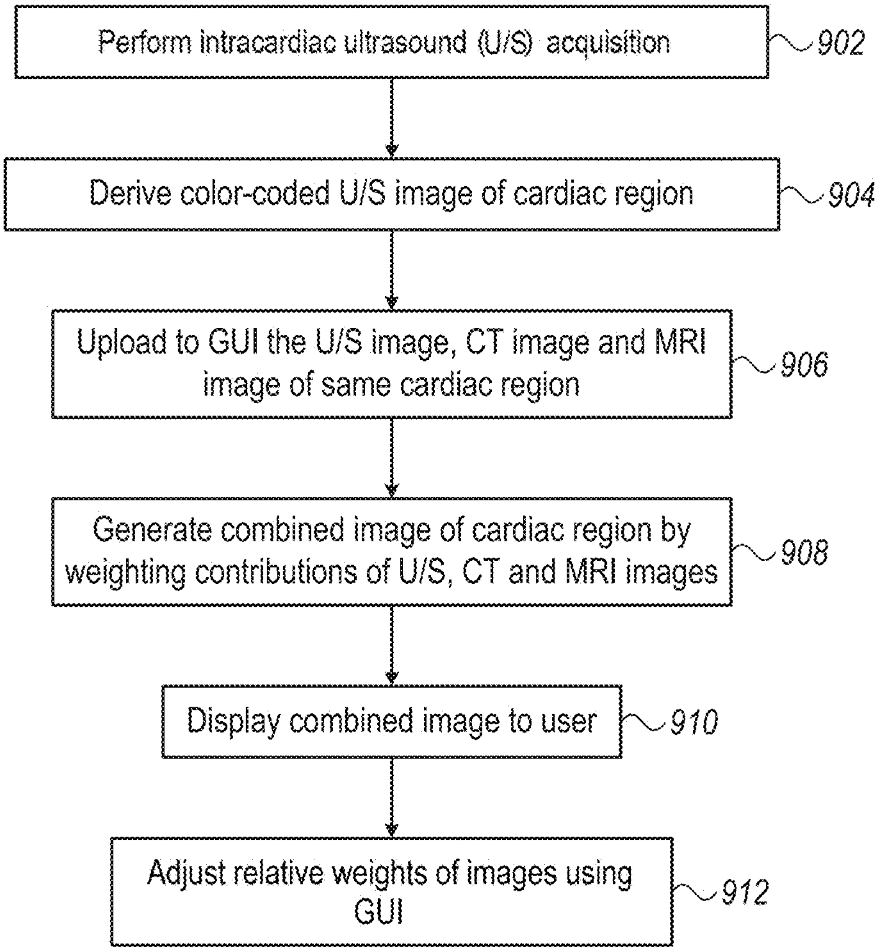
FIG. 9 is a flow chart that schematically illustrates a method for deriving and displaying the results of FIG. 5, in accordance with an embodiment of the present invention.

FIG. 9 is a flow chart that schematically illustrates a method for deriving and displaying the results of FIG. 5, in accordance with an embodiment of the present invention. The procedure begins by performing an ultrasound (US) acquisition of a cardiac region, such as inside a cardiac chamber, such as shown in FIG. 1, at a 4D ultrasound acquisition step 902.

Next, processor 39 derives a color-coded US image, such as image 502, of a cardiac region, at an ultrasound imaging step 904.

At images uploading step 906, processor 39 uploads to GUI 500 US image 502, CT image 504, and MRI image 506. The images comprise a same cardiac region and are registered one with other by processor 39.

At a combined image generation step 908, processor 39 generates combined image 508 by weighing US image 502, CT image 504, and MRI image 506, using one of the normalizing weighting methods described above.

At a displaying step 910, processor 39 displays combined image 508 to a user.

Finally, at an adjustment step 912, the user adjusts the relative weights (e.g., contributions) of images 502 using GUI 500, 504, and 506, $\omega_{U/S}$, $\omega_{CT}$, and $\omega_{MRI}$, respectively, by moving a cursor in GUI 500, as described above, to make combined image 508 more informative.

Although the embodiments described herein mainly address cardiac applications, the methods and systems described herein can also be used in other body organs. For example, the disclosed technique can be used with transesophageal ultrasound (TEE) devices visualizing the heart. As another example, the disclosed technique may be used for invasive ultrasound lung imaging, and for visualizing liver and kidney.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:

a four-dimensional (4D) intracardiac ultrasound probe for insertion into a heart, the ultrasound probe comprising:

a two-dimensional (2D) ultrasound transducer array configured to produce a time series of three-dimensional (3D) ultrasound images of a volume of the heart; and a sensor configured to output signals indicative of a position, direction and orientation of the 2D ultrasound transducer array inside the heart; and a processor, which is configured to:

using the signals output by the sensor, register multiple ultrasound images of a region of the heart, acquired simultaneously by the 2D ultrasound transducer array, with one another;

extend a simulated beam ray from a point selected by a user to a center mass of the heart, such that the simulated beam ray intersects a first surface comprising at least one of a plurality of inner wall images and then intersects a second surface comprising at least one of a plurality of outer wall images;

isolate the plurality of inner wall images and the plurality of outer wall images of the region from each other, wherein the plurality of inner wall images and the plurality of outer wall images of the region are endocardium images and respective epicardium images of a same portion of the heart;

apply different graphical encodings to the plurality of inner wall images and the plurality of outer wall images, wherein the different graphical encodings comprise different color palettes being applied to each of the plurality of inner and outer wall images;

overlay the plurality of inner wall images and the plurality of outer wall images to generate a combined image;

display the combined image to the user; and adjust a transparency of one or both of the overlaid plurality of inner wall images and outer wall images.

2. A method, comprising:

inserting a four-dimensional (4D) intracardiac into a heart, an ultrasound probe comprising:

a two-dimensional (2D) ultrasound transducer array configured to produce a time series of three-dimensional (3D) ultrasound images of a volume of the heart; and a sensor configured to output signals indicative of a position, direction and orientation of the 2D ultrasound transducer array inside the heart;

using the signals output by the sensor, registering multiple ultrasound images of a region of the heart, acquired simultaneously by the 2D ultrasound transducer array, with one another;

extending a simulated beam ray from a point selected by a user to a center mass of the heart, such that the simulated beam ray intersects a first surface comprising at least one of a plurality of inner wall images and then intersects a second surface comprising at least one of a plurality of outer wall images;

isolating the plurality of inner wall images and the plurality of outer wall images of the region from each other, wherein the plurality of inner wall images and the plurality of outer wall images of the region are endocardium images and respective epicardium images of a same portion of the heart;

applying different graphical encodings to the plurality of inner wall images and the plurality of outer wall images, wherein the different graphical encodings comprise different color palettes being applied to each of the plurality of inner and outer wall images;

overlaying the plurality of inner wall images and the plurality of outer wall images to generate a combined image;

displaying the combined image to the user; and adjusting a transparency of one or both of the overlaid plurality of inner wall images and outer wall images.

3. A system, comprising:

a four-dimensional (4D) ultrasound probe for insertion into an organ, the ultrasound probe comprising:

a two-dimensional (2D) ultrasound transducer array configured to produce a time series of three-dimensional (3D) ultrasound images of a volume of the organ; and a sensor configured to output signals indicative of a position, direction and orientation of the 2D ultrasound transducer array inside the organ; and a processor, which is configured to:

using the signals output by the sensor, register multiple ultrasound images of a region of the organ, acquired simultaneously by the 2D ultrasound transducer array, with one another;

extend a simulated beam ray from a point selected by a user to a center mass of the organ, such that the simulated beam ray intersects a first surface comprising at least one of a plurality of inner wall images and then intersects a second surface comprising at least one of a plurality of outer wall images;

isolate the plurality of inner wall images and the plurality of outer wall images of the region from each other, wherein the plurality of inner wall images and the plurality of outer wall images of the region are inner tissue images and respective outer tissue images of a same portion of the organ;

apply different graphical encodings to the plurality of inner wall images and the plurality of outer wall images, wherein the different graphical encodings comprise different color palettes being applied to each of the plurality of inner and outer wall images;

overlay the plurality of inner wall images and the plurality of outer wall images to generate a combined image;

display the combined image to the user; and adjust a transparency of one or both of the overlaid plurality of inner wall images and outer wall images.

* * * * *